(12) United States Patent
Jeng et al.

(10) Patent No.: US 11,746,083 B2
(45) Date of Patent: Sep. 5, 2023

(54) COMPOUND, RESIN COMPOSITION AND LAMINATED SUBSTRATE THEREOF

(71) Applicant: Industrial Technology Research Institute, Hsinchu (TW)

(72) Inventors: Jyh-Long Jeng, New Taipei (TW); Jeng-Yu Tsai, Chiayi (TW); Wei-Ta Yang, Taoyuan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 154 days.

(21) Appl. No.: 17/138,254

(22) Filed: Dec. 30, 2020

(65) Prior Publication Data

US 2022/0204442 A1  Jun. 30, 2022

(51) Int. Cl.
*C08G 18/78* (2006.01)
*C07C 271/58* (2006.01)
*C08G 18/34* (2006.01)

(52) U.S. Cl.
CPC ............ *C07C 271/58* (2013.01); *C08G 18/34* (2013.01); *C08G 18/7812* (2013.01)

(58) Field of Classification Search
CPC ............ C08G 18/7812; C08G 18/3814; C07C 271/58
See application file for complete search history.

(56) References Cited

U.S. PATENT DOCUMENTS 9,850,401 B2    12/2017  Lai et al.
2007/0166559 A1*  7/2007  Tai .................... H05K 1/0346
                                                428/458

(Continued)

FOREIGN PATENT DOCUMENTS

CN    1968982 A    5/2007
CN   102471460 A   5/2012

(Continued)

OTHER PUBLICATIONS

Michael Szycher. Jul. 13, 2012, Structure-Property Relations in Polyurethanes from: Szycher's Handbook of Polyurethanes CRC Press.*

(Continued)

*Primary Examiner* — Michael L Leonard
(74) *Attorney, Agent, or Firm* — Birch, Stewart, Kolasch & Birch, LLP

(57) ABSTRACT

A compound, a resin composition and a laminated substrate thereof are provided. The compound has a structure represented by Formula (I)

Formula (I)

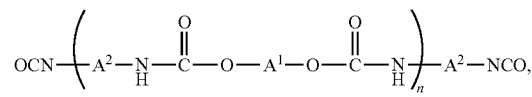

wherein $A^1$ is $C_{24\text{-}48}$ alkylene group, $C_{24\text{-}48}$ alkenylene group, $C_{24\text{-}48}$ alkynylene group, $C_{24\text{-}48}$ alicyclic alkylene group, $C_{24\text{-}48}$ alicyclic alkenylene group, or $C_{24\text{-}48}$ alicyclic alkynylene group. $A^2$ is $C_{2\text{-}12}$ alkylene group, $C_6$-$C_{25}$ arylene group with two reactive groups, $C_{4\text{-}8}$ cycloalkylene group, $C_{5\text{-}25}$ heteroarylene group, divalent $C_7$-$C_{25}$ alkylaryl group, divalent $C_{7\text{-}25}$ acylaryl group, divalent $C_{6\text{-}25}$ aryl ether group, or divalent $C_{7\text{-}25}$ acyloxyaryl group; and, $n \geq 1$.

15 Claims, 1 Drawing Sheet

(56) References Cited

U.S. PATENT DOCUMENTS

| | | | |
|---|---|---|---|
| 2009/0240019 A1* | 9/2009 | Inoue | C08G 18/4277 |
| | | | 528/59 |
| 2012/0302676 A1 | 11/2012 | Oya et al. | |
| 2015/0159043 A1 | 6/2015 | Lai et al. | |
| 2017/0009017 A1 | 1/2017 | Huang et al. | |
| 2017/0183470 A1 | 6/2017 | Chou et al. | |
| 2017/0210854 A1 | 7/2017 | Matsuyama et al. | |

FOREIGN PATENT DOCUMENTS

| | | | |
|---|---|---|---|
| JP | 2010-70757 A | 4/2010 | |
| JP | 2011-94037 A | 5/2011 | |
| TW | 201113312 A1 | 4/2011 | |
| TW | 201500409 A | 1/2015 | |
| TW | I493007 B | 7/2015 | |
| TW | 201825295 A | 7/2018 | |
| TW | I634988 B | 9/2018 | |
| TW | 202037628 A | 10/2020 | |
| WO | WO-2020158360 A1 * | 8/2020 | C08G 18/34 |

OTHER PUBLICATIONS

WO-2020158360_08-2020_English Translation.*
Hasegawa et al., "Poly(ester imide)s possessing low coefficients of thermal expansion (CTE) and low water absorption (III). Use of bis(4-aminophenyl)terephthalate and effect of substituents", European Polymer Journal, vol. 46, 2010, pp. 1510-1524.
Taiwanese Office Action and Search Report for Taiwanese Application No. 110116722, dated Nov. 8, 2021.
Office Action issued in Chinese Patent Application No. 202110435689.0, dated May 28, 2023.

* cited by examiner

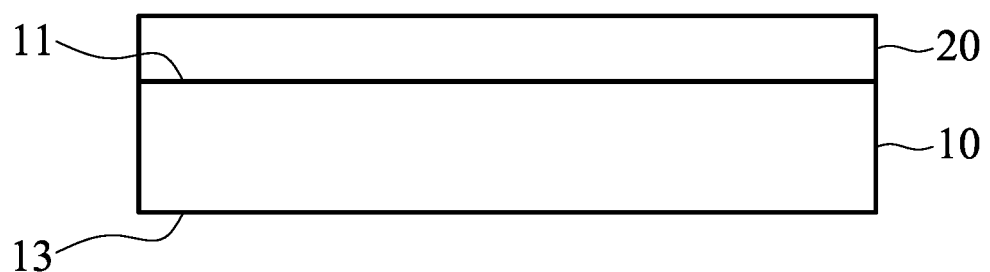

COMPOUND, RESIN COMPOSITION AND LAMINATED SUBSTRATE THEREOF

TECHNICAL FIELD

The disclosure relates to a compound, a resin composition and a laminated substrate thereof.

BACKGROUND

Consumers are demanding wider application of high-frequency, high-speed transmission, and so the required specifications for PCB materials are constantly being updated. Due to its excellent thermal stability and good mechanical, electrical, and chemical properties, polyimide (PI) is widely used in printed circuit boards.

The cured product of conventional polyimide resin, however, exhibits a high moisture absorption rate due to the polarity of the amide skeleton, resulting in the dielectric loss factor (Df) of the cured product of conventional polyimide resin increasing during operation in a humid atmosphere. In addition, although reducing the surface roughness of the copper foil can reduce the transmission loss of the high-frequency signal and meet the needs of high-frequency signal transmission, the bonding strength between the copper foil and the circuit substrate would also be reduced, thereby causing the copper foil to peel off of the circuit substrate easily and decreasing the reliability of printed circuit boards. Due to the low dielectric coefficient and low dielectric loss factor, liquid-crystal polymer (LCP) can serve as materials of high frequency circuit board. However, the layer made of liquid-crystal polymer is easy to peel off of the copper foil, since adhesion between the layer made of liquid-crystal polymer and the copper foil is poor.

SUMMARY

The disclosure provides a compound. According to embodiments of the disclosure, the compound has a structure represented by Formula (I):

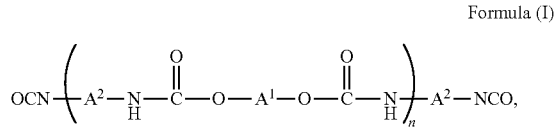

Formula (I)

herein $A^1$ can be $C_{24-48}$ alkylene group, $C_{24-48}$ alkenylene group, $C_{24-48}$ alkynylene group, $C_{24-48}$ alicyclic alkylene group, $C_{24-48}$ alicyclic alkenylene group, or $C_{24-48}$ alicyclic alkynylene group; $A^2$ can be $C_{2-12}$ alkylene group, $C_{6-25}$ arylene group, $C_{4-8}$ cycloalkylene group, $C_{5-25}$ heteroarylene group, divalent $C_{7-25}$ alkylaryl group, divalent $C_{7-25}$ acylaryl group, divalent $C_{6-25}$ aryl ether group, or divalent $C_{7-25}$ acyloxyaryl group; and, $n \geq 1$.

According to embodiments of the disclosure, the disclosure provides a resin composition. According to embodiments of the disclosure, the resin composition includes the aforementioned compound, and an anhydride, wherein the anhydride includes monoanhydride, dianhydride, or a combination thereof.

According to embodiments of the disclosure, the disclosure also provides a laminated substrate. According to embodiments of the disclosure, the laminated substrate includes a conductive layer having a surface; and, a layer. The layer is disposed on the surface of the conductive layer, wherein the layer includes the cured product of the aforementioned resin composition.

A detailed description is given in the following embodiments with reference to the accompanying drawings.

BRIEF DESCRIPTION OF THE DRAWINGS

The FIGURE is a schematic view of a laminated substrate according to an embodiment of the disclosure.

DETAILED DESCRIPTION

The compound, resin composition and laminated substrate of the disclosure are described in detail in the following description. In the following detailed description, for purposes of explanation, numerous specific details and embodiments are set forth in order to provide a thorough understanding of the present disclosure. The specific elements and configurations described in the following detailed description are set forth in order to clearly describe the present disclosure. It will be apparent, however, that the exemplary embodiments set forth herein are used merely for the purpose of illustration, and the inventive concept may be embodied in various forms without being limited to those exemplary embodiments. As used herein, the term "about" in quantitative terms refers to plus or minus an amount that is general and reasonable to persons skilled in the art.

As used herein, the term "about" in quantitative terms refers to plus or minus an amount that is general and reasonable to persons skilled in the art.

Moreover, the use of ordinal terms such as "first", "second", "third", etc., in the disclosure to modify an element does not by itself connote any priority, precedence, or order of one claim element over another or the temporal order in which it is formed, but are used merely as labels to distinguish one claim element having a certain name from another element having the same name (but for use of the ordinal term) to distinguish the claim elements.

The disclosure provides a compound, resin composition, and laminated substrate. According to embodiments of the disclosure, the resin composition can be applied to form a polyimide layer (or polyurethane-polyimide layer). Since the resin composition includes the compound with specific structure and has a specific proportion of the components, the layer (i.e. the cured product) prepared by the resin composition not only exhibits low-k dielectric (Dk), low dielectric loss (Df) at high frequency (at more than 10 GHz) and stable dielectric characteristic (after water adsorption), but also great adhesive strength, thermal tolerance and chemical resistance after coating on a metal foil substrate.

According to embodiments of the disclosure, the compound can have a structure represented by Formula (I):

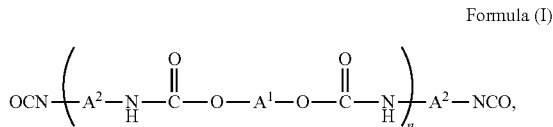

Formula (I)

wherein $A^1$ can be $C_{24-48}$ alkylene group, $C_{24-48}$ alkenylene group, $C_{24-48}$ alkynylene group, $C_{24-48}$ alicyclic alkylene group, $C_{24-48}$ alicyclic alkenylene group, or $C_{24-48}$ alicyclic alkynylene group; $A^2$ can be $C_{2-12}$ alkylene group, $C_{6-25}$ arylene group, $C_{4-8}$ cycloalkylene group, $C_{5-25}$ heteroarylene group, divalent $C_{7-25}$ alkylaryl group, divalent $C_{7-25}$ acylaryl group, divalent $C_{6-25}$ aryl ether group, or divalent $C_{7-25}$ acyloxyaryl group; and, n can be greater than or equal to 1, such as 1, 2, 3, 4, 5, 6, 7, 8, 9, 10, 15, 20, 25, 30 or 50. According to embodiments of the disclosure, the hydrogen bonded with the carbon of $A^1$ and $A^2$ can be optionally replaced with fluorine, $C_{1-6}$ alkyl group, or $C_{1-6}$ fluoroalkyl group.

According to embodiments of the disclosure, $A^1$ of the first repeating unit can be a linear group, branched group, or branched cyclic group, and A1can have a chemical formula of —$C_nH_{2n}$—, —$C_nH_{2(n-1)}$—, —$C_nH_{2(n-2)}$—, —$C_nH_{2(n-3)}$—, —$C_nH_{2(n-4)}$—, —$C_nH_{2(n-5)}$—, or —$C_nH_{2(n-6)}$—, wherein n is 24 to 48 (such as 25, 26, 27, 28, 29, 30, 31, 32, 33, 34, 35, 36, 37, 38, 39, 40, 41, 42, 43, 44, 45, 46, or 47).

According to embodiments of the disclosure, A can be

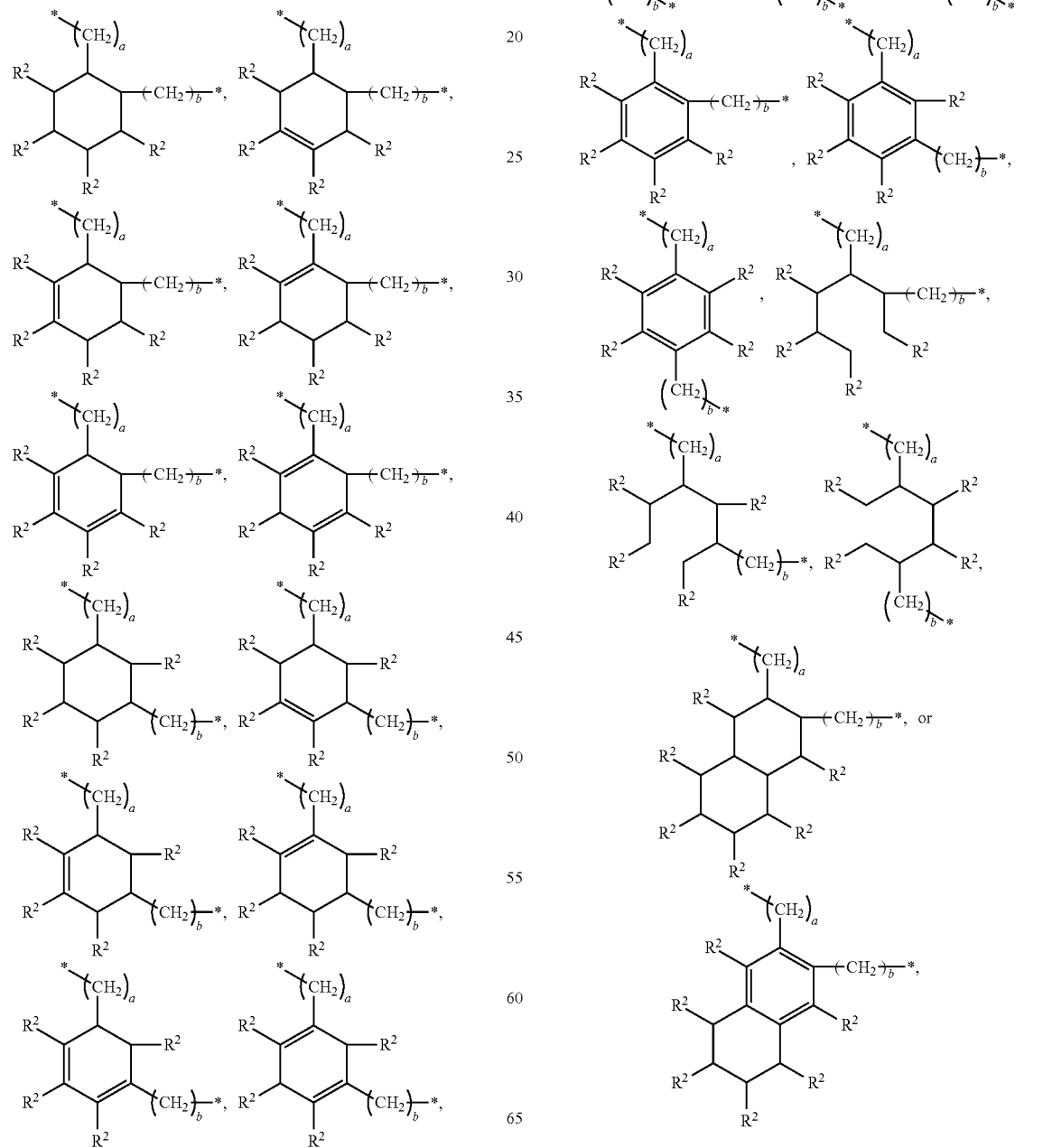

wherein $A^1$ is connected to oxygen by the location represented by *. $12 \geq a \geq 4$; $12 \geq b \geq 4$; $R^2$ are independently hydrogen, $C_{4-10}$ alkyl group, $C_{4-10}$ alkenyl, or $C_{4-10}$ alkynyl; at least two $R^2$ are not hydrogen; and, $A^1$ has 24-48 carbon atoms. According to embodiments of the disclosure, at least two $R^2$ of each $A^1$ are not hydrogen (i.e. at least two $R^2$ are independently $C_{4-10}$ alkyl group, $C_{4-10}$ alkenyl group, or $C_{4-10}$ alkynyl group). According to embodiments of the disclosure, at least three $R^2$ of each $A^1$ are not hydrogen (i.e. at least three $R^2$ are independently $C_{4-10}$ alkyl group, $C_{4-10}$ alkenyl group, or $C_{4-10}$ alkynyl group). According to embodiments of the disclosure, $A^1$ can be

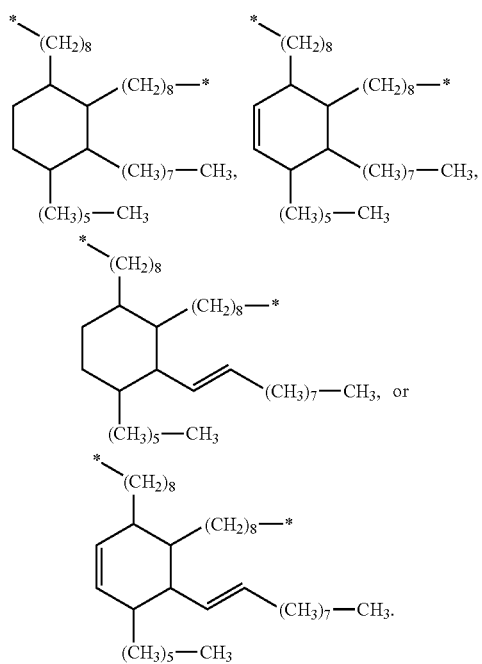

According to embodiments of the disclosure, the $A^2$ can be

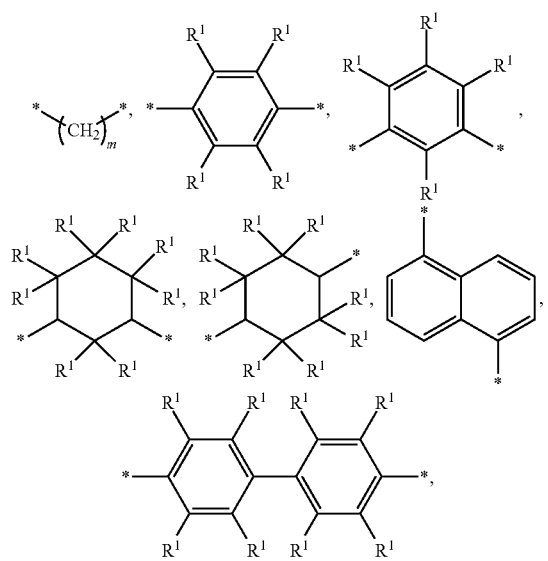

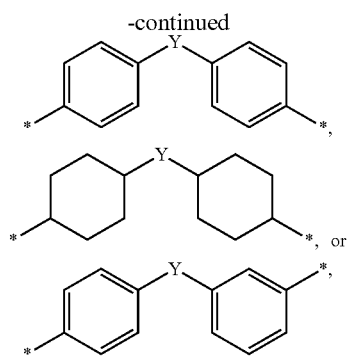

wherein A is connected to nitrogen by the location represented by *. Y can be —O—, —C($R^1$)$_2$—,

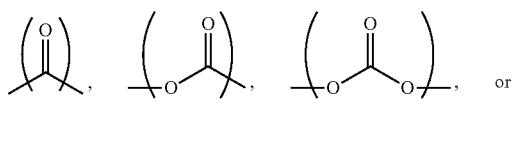

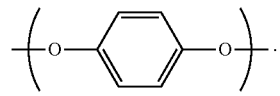

$R^1$ can be independently hydrogen, fluorine, $C_{1-6}$ alkyl group, or $C_{1-6}$ fluoroalkyl group; and, m can be 2, 3, 4, 5, 6, 7, or 8.

According to embodiments of the disclosure, $C_{1-10}$ alkyl group can be linear or branched alkyl group. For example, $C_{1-10}$ alkyl group can be methyl, ethyl, propyl, butyl, pentyl, hexyl, heptyl, octyl, or an isomer thereof. According to embodiments of the disclosure, $C_{1-6}$ fluoroalkyl group can be an alkyl group which a part of or all hydrogen atoms bonded on the carbon atom are replaced with fluorine atoms, and $C_{1-6}$ fluoroalkyl group can be linear or branched, such as fluoromethyl, fluoroethyl, fluoropropyl, fluorobutyl, fluoropentyl, fluorohexyl, or an isomer thereof. Herein, fluoromethyl group can be monofluoromethyl group, difluoromethyl group or trifluoromethyl group, and fluoroethyl can be monofluoroethyl group, difluoroethyl group, trifluoroethyl group, tetrafluoroethyl, or perfluoroethyl.

According to embodiments of the disclosure, alkylene group can be linear or branched alkylene group. According to embodiments of the disclosure, alkenyl can be linear or branched alkenyl. According to embodiments of the disclosure, alkynyl can be linear or branched alkynyl.

According to embodiments of the disclosure, the compound of the disclosure can be prepared by reacting a dihydric alcohol with a diisocyanate. According to embodiments of the disclosure, the dihydric alcohol can have a chemical formula of $C_nH_{2(n+1)}O_2$, $C_nH_{2(n)}O_2$, $C_nH_{2(n-1)}O_2$, $C_nH_{2(n-2)}O_2$, $C_nH_{2(n-3)}O_2$, $C_nH_{2(n-4)}O_2$, or $C_nH_{2(n-5)}O_2$—, wherein n can be 24 to 48(such as 25, 26, 27, 28, 29, 30, 31, 32, 33, 34, 35, 36, 37, 38, 39, 40, 41, 42, 43, 44, 45, 46, or 47). For example, the dihydric alcohol can be

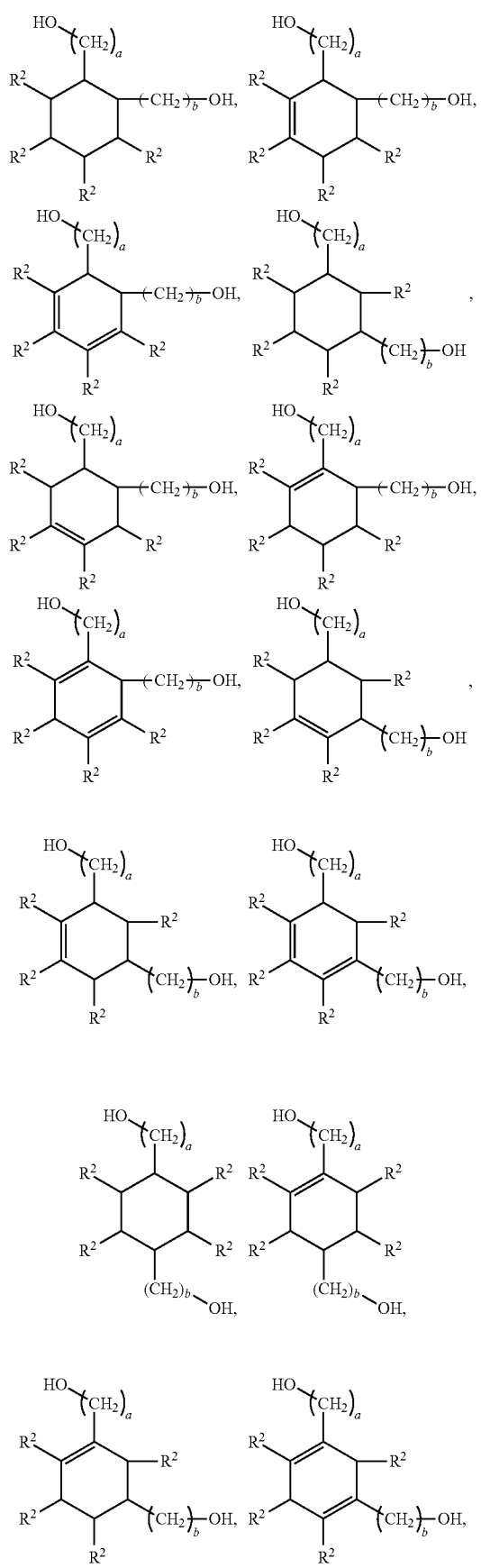
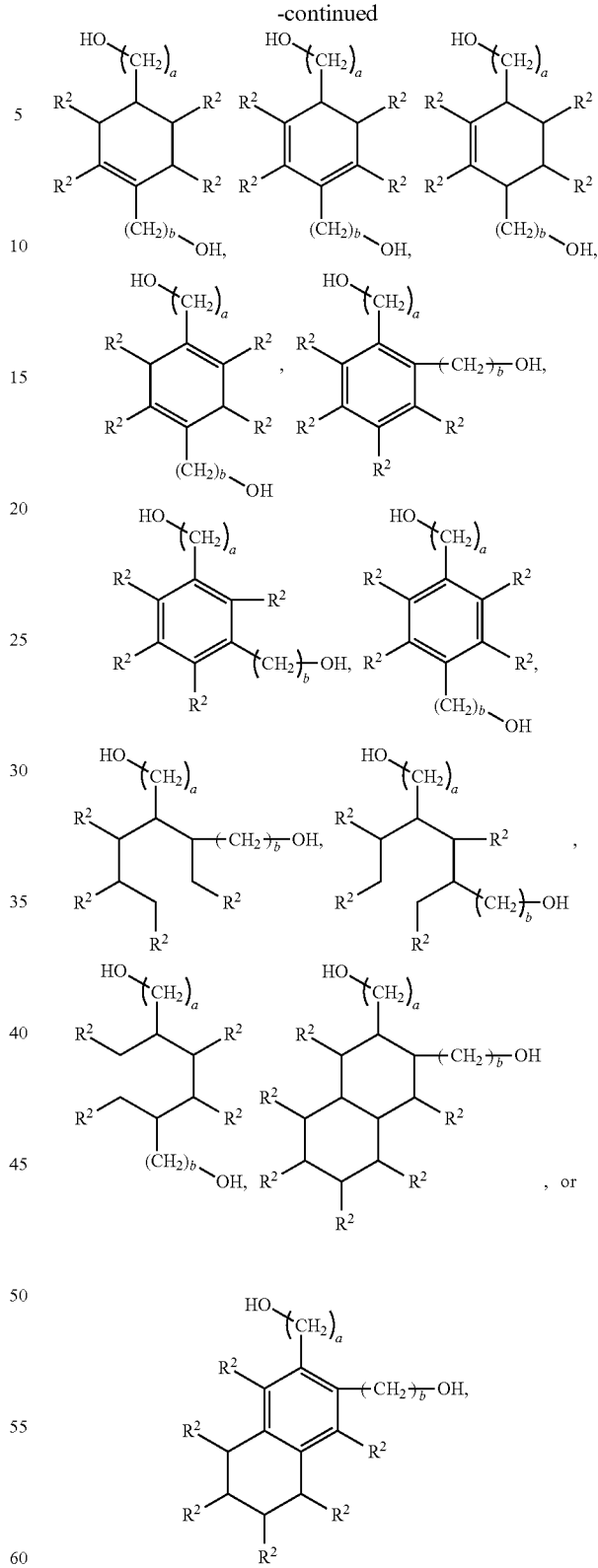
wherein 12≥a≥4; 12≥b≥4; and, $R^2$ are independently hydrogen, $C_{4-10}$ alkyl group, $C_{4-10}$ alkenyl, or $C_{4-10}$ alkynyl, and at least two $R^2$ are not hydrogen. According to embodiments of the disclosure, the dihydric alcohol has 24-48 carbon atoms.

According to embodiments of the disclosure, the diisocyanate can be

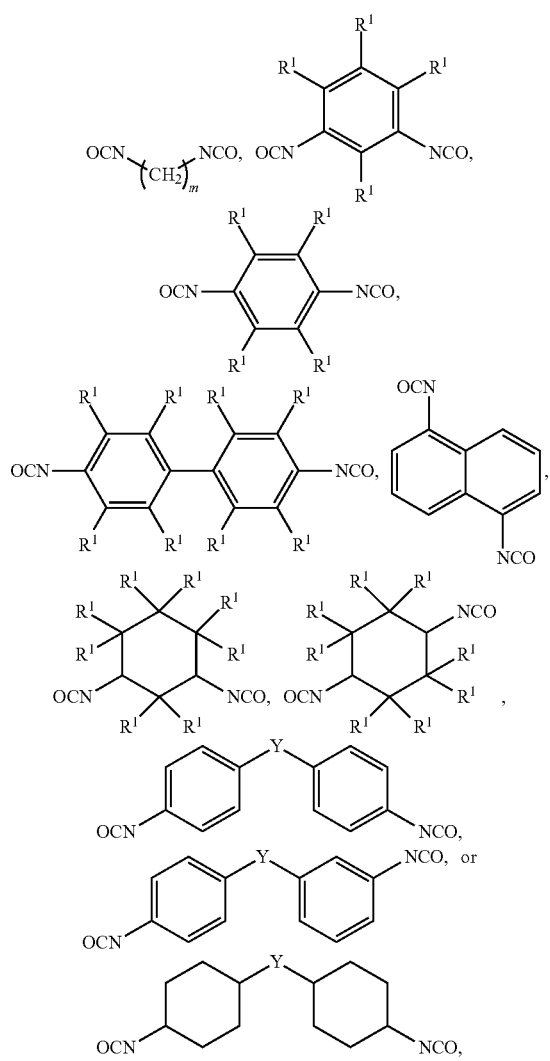

wherein Y can be —O—, —C(R¹)₂—,

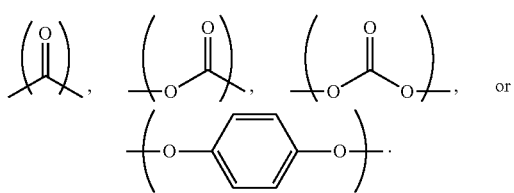

or

R¹ can be independently hydrogen, fluorine, C₁₋₆ alkyl group, or C₁₋₆ fluoroalkyl group; and, m can be 2, 3, 4, 5, 6, 7, or 8. According to embodiments of the disclosure, the diisocyanate can be pentamethylene diisocyanate, hexamethylene diisocyanate (HDI), 4,4'-methylene diphenyl diisocyanate (MDI), 4,4'-methylene dicyclohexyl diisocyanate (H12MDI), 2,4-toluene diisocyanate, 2,5-toluene diisocyanate, 2,6-toluene diisocyanate, isophorone diisocyanate (IPDI), 1,5-naphthalene diisocyanate (NDI), p-phenylene diisocyanate (PPDI), xylylene diisocyanate (XDI), hydrogenated 1,4-xylylene diisocyanate (1,4-H6XDI), or trimethyl hexamethylene diisocyanate (TMDI). According to embodiments of the disclosure, the molar ratio of diisocyanate to dihydric alcohol can be about 1.05 to 2.

According to embodiments of the disclosure, the disclosure also provides a resin composition, which can be used to prepare a polyimide layer or polyurethane-polyimide layer. According to embodiments of the disclosure, the resin composition includes the compound of Formula (I) of the disclosure and an anhydride. According to embodiments of the disclosure, the anhydride includes monoanhydride, dianhydride, or a combination thereof.

According to embodiments of the disclosure, the monoanhydride can be maleic anhydride, succinic anhydride, styrene maleic anhydride, 5-norbornene-2,3-dicarboxylanhydride, 3,6-epoxy-1,2,3,6-tetra hydrophthalicanhydride, 3,4,5,6-tetrahydrophthalic anhydride, phthalic anhydride, 1,2,3,6-tetrahydrophthalic anhydride, itaconic anhydride (IA), citraconic anhydride (CA), or 2,3-dimethylmaleic anhydride (DMMA). According to embodiments of the disclosure, the dianhydride can be

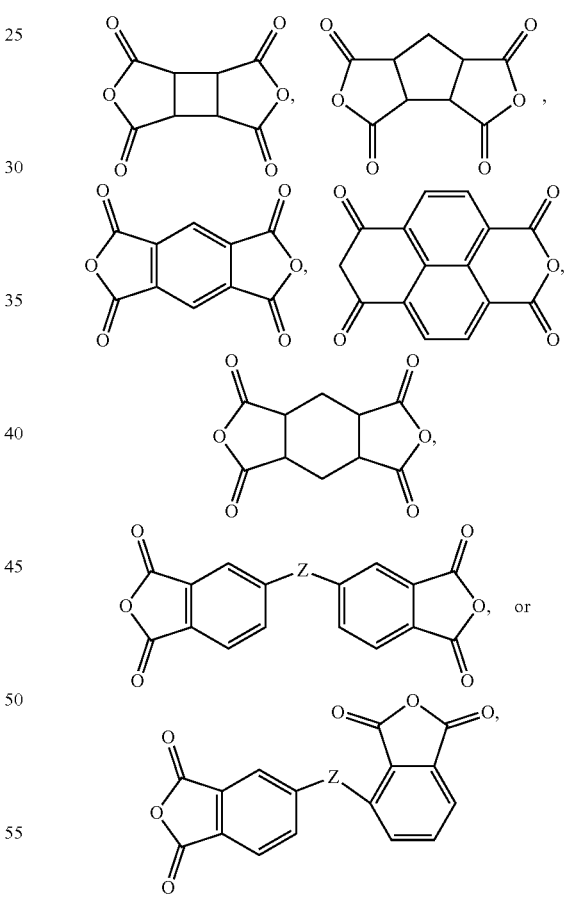

wherein Z is single bond, —O—, —SO₂—, —C(CH₃)₂—, —C(CF₃)₂—,

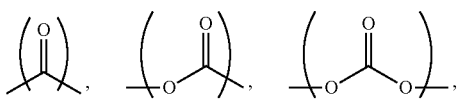

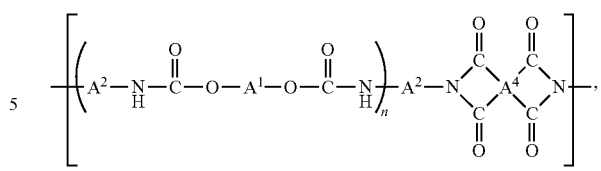

wherein $A^1$, $A^2$, and n are the same as defined above; and, $A^4$ can be

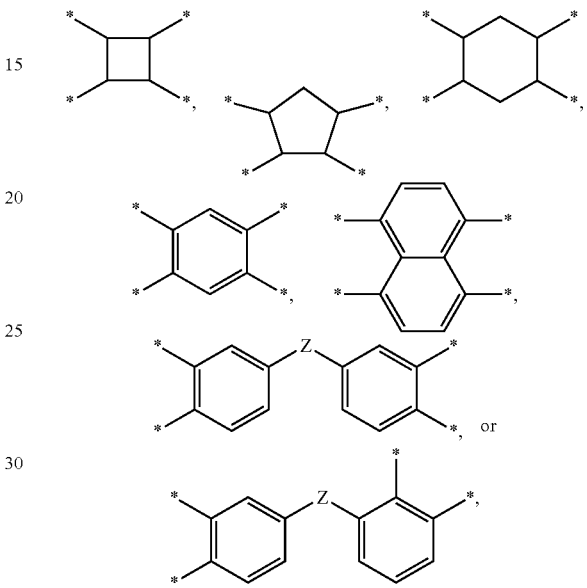

wherein $A^4$ is connected to carbonyl group by the location represented by *. Z is single bond, —O—, —SO$_2$—, —C(CH$_3$)$_2$—, —C(CF$_3$)$_2$—,

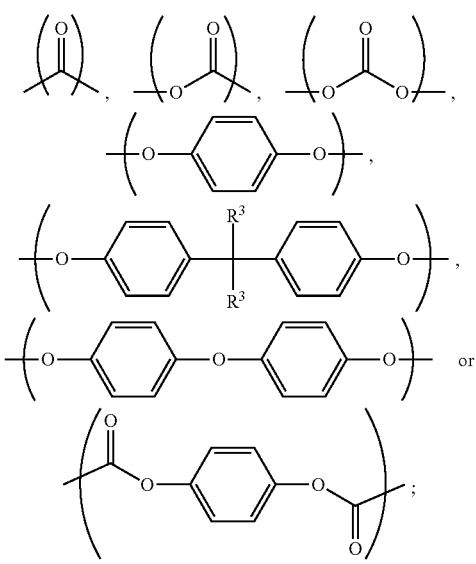

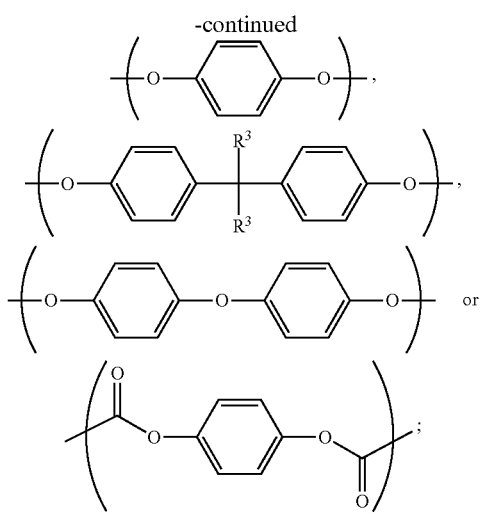

and, $R^3$ are independently hydrogen, $C_{1-6}$ alkyl group, or $C_{1-6}$ fluoroalkyl group. According to embodiments of the disclosure, the dianhydride can be pyromellitic dianhydride (PMDA), 4,4'-(hexafluoroisopropylidene)-diphthalic anhydride (6FDA), 4,4'-oxydiphthalic anhydride (ODPA), 1,3-bis(4-aminophenoxy)benzene (RODA), 4,4'-biphthalic dianhydride (BPDA), 4,4'-bisphenol A dianhydride (BPADA), p-phenylene bis(trimellitate) dianhydride (TAHQ), or hydroquinnone diphtalic anhydride (HQDA).

According to embodiments of the disclosure, the anhydride can be monoanhydride, and the resin composition includes the compound of Formula (I) and monoanhydride. The anhydride can have a mole number $M^1$, and the compound can have a mole number $M^2$, wherein $1.5 \leq M^2/M^1 \leq 2.5$. According to embodiments of the disclosure, the compound prepared by the resin composition can be

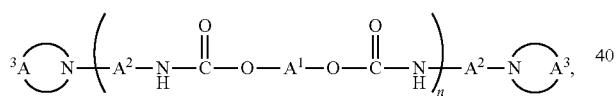

wherein $A^1$, $A^2$, and n are the same as defined above. $A^3$ can be a moiety eliminating oxygen atom from a monoanhydride, and $A^3$ is connected to nitrogen via two carbonyl groups. For example, the compound prepared from the resin composition can be

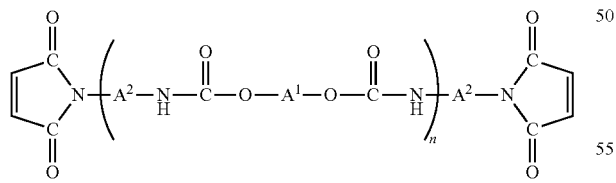

(i.e. the monoanhydride can be maleic anhydride).

According to embodiments of the disclosure, the anhydride can be dianhydride, and the resin composition includes the compound of Formula (I) and dianhydride. According to embodiments of the disclosure, the anhydride can have a mole number $M^1$, and the compound has a mole number $M^2$, wherein $0.05 \leq M^2/M^1 \leq 1$. According to embodiments of the disclosure, the polyimide prepared from the resin composition can have a repeating unit, wherein the structure of the repeating unit can be and, $R^3$ can be hydrogen, fluorine, $C_{1-6}$ alkyl group, or $C_{1-6}$ fluoroalkyl group.

According to embodiments of the disclosure, when the anhydride is a combination of monoanhydride and dianhydride, the anhydride has a mole number $M^1$, and the compound has a mole number $M^2$, wherein $0.05 \leq M^2/M^1 \leq 3$, and the molar ratio of the monoanhydride to the dianhydride can be 1:99 to 99:1.

According to embodiments of the disclosure, when the resin composition includes the compound of Formula (I) and dianhydride, the resin composition can further include a diamine compound. According to embodiments of the disclosure, the anhydride (i.e. dianhydride) has a mole number $M^1$, the compound has a mole number $M^2$, and the diamine compound has a mole number $M^3$, wherein $0.5 \leq (M^2+M^3)/M^1 \leq 3$. In addition, According to embodiments of the disclosure, $0.05 \leq M^2/(M^2+M^3) \leq 0.3$. When $M^2/(M^2+M^3)$ is too low, adhesion between the layer prepared by the resin composition (i.e. the cured product) and the metal foil substrate is obviously deteriorated. When $M^2/(M^2+M^3)$ is too high, the layer prepared from the resin composition (i.e. the cured product) exhibits poor chemical resistance. According to embodiments of the disclosure, the polymer prepared from the resin composition (such as polyurethane-polyimide) can have a first repeating unit and a second repeating unit, wherein the structure of the first repeating unit can be

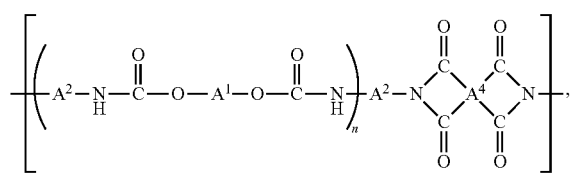

and the structure of the second repeating unit can be

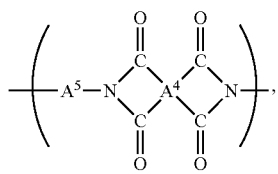

wherein $A^1$, $A^2$, $A^4$, and n are the same as defined above; and, $A^5$ can be

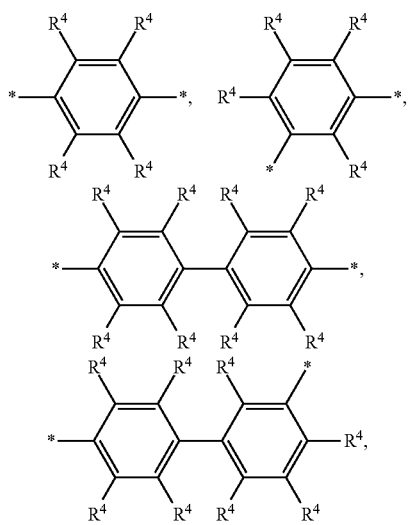

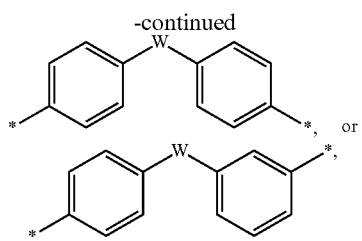

wherein $A^5$ is connected to nitrogen (which is nitrogen of the first repeating unit or the second repeating unit) by the location represented by *. W can be —O—, —C(CH$_3$)$_2$—, —C(CF$_3$)$_2$—,

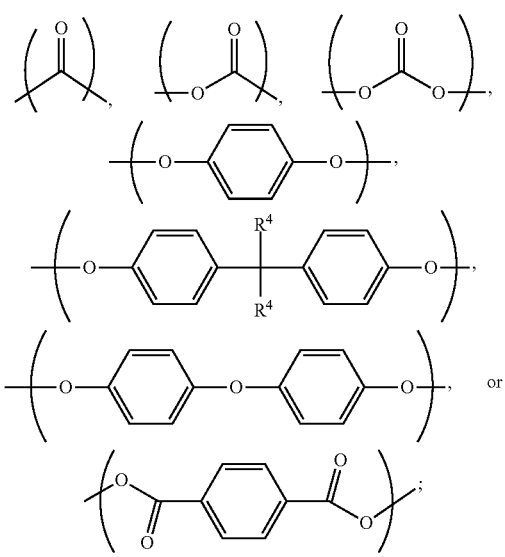

and, $R^4$ can be hydrogen, fluorine, $C_{1-6}$ alkyl group, or $C_{1-6}$ fluoroalkyl group. According to embodiments of the disclosure, the number ratio of the first repeating unit to the second repeating unit can be 1:19 to 3:7. When the number ratio of the first repeating unit to the second repeating unit is too low, the adhesion between the layer prepared by the resin composition (i.e. the cured product) and the metal foil substrate is obviously deteriorated. When the number ratio of the first repeating unit to the second repeating unit is too high, the layer prepared from the resin composition (i.e. the cured product) exhibits poor chemical resistance.

According to embodiments of the disclosure, the diamine compound can be

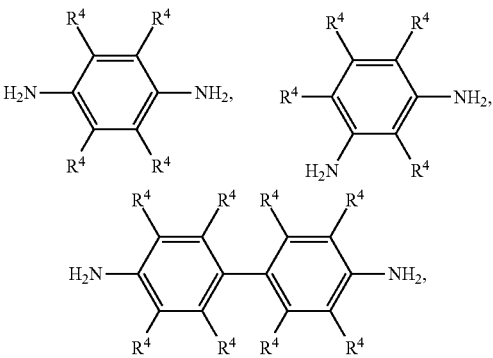

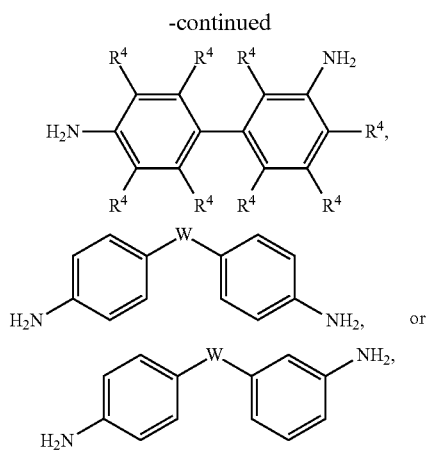

wherein Y can be —O—, —C(CH$_3$)$_2$—, —C(CF$_3$)$_2$—,

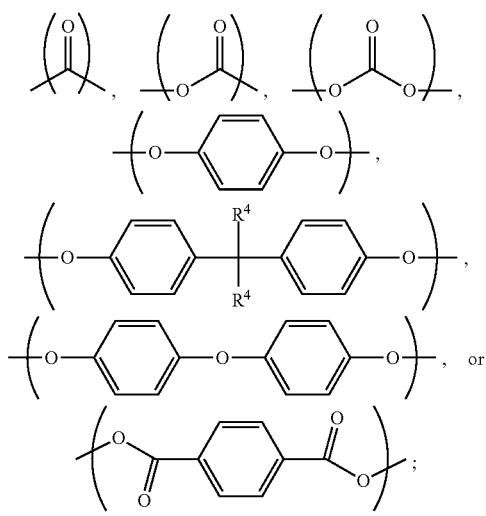

and, R$^4$ can be hydrogen, fluorine, C$_{1-6}$ alkyl group, or C$_{1-6}$ fluoroalkyl group. According to embodiments of the disclosure, the diamine compound can be m-tolidine (m-TB), m-phenylenediamine (m-PDA), p-phenylenediamine (p-PDA), 4,4'-oxydianiline (4,4'-ODA), 3,4'-oxydianiline (3,4'-ODA), 1,4-bis(4-aminophenoxy)benzene (1,4-APB), 1,3-bis(4-aminophenoxy)benzene (1,3-APB), 1,2-bis(4-aminophenoxy)benzene (1,2-APB), 1,3-bis(3-aminophenoxy)benzene (APB-133), 2,5-bis(4-aminophenoxy)toluene, bis(4-[4-aminophenoxy]phenyl)ether (BAPE), 4,4'-bis[4-aminophenoxy]biphenyl (BAPB), 2,2-bis[4-(4-aminophenoxy)]phenyl propane (BAPP), bis-(4-(4-aminophenoxy)phenyl sulfone (BAPS), 2,2'-bis (trifluoromethyl) 4,4'-diaminobiphenyl (TFMB), 1,4-diaminobenzene (PPD), or a combination thereof According to embodiments of the disclosure, when the resin composition simultaneously includes the compound of Formula (I), monoanhydride, and dianhydride, the resin composition can further include a diamine compound. According to embodiments of the disclosure, the anhydride (i.e. monoanhydride and dianhydride) can have a mole number M$^1$, the compound has a mole number M$^2$, and the diamine compound has a mole number M$^3$, wherein $0.5 \leq (M^2+M^3)/M^1 \leq 3$. According to embodiments of the disclosure, the polymer prepared from the resin composition (such as polyurethane-polyimide) can have a structure represented by

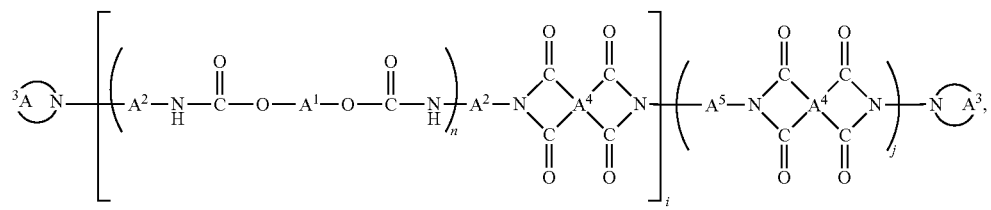

wherein A$^1$, A$^2$, A$^3$, A$^4$, A$^5$ and n are the same as defined above, i≥1 (such as 100≥i≥1), j≤1 (such as 100≥j≥1), and i:j can be 1:19 to 19:1. According to embodiments of the disclosure, repeating unit

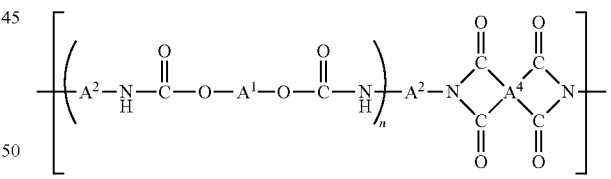

and repeating unit

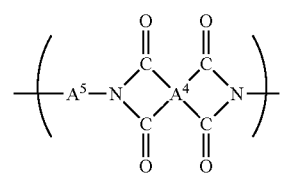

are arranged in a random or block fashion. According to embodiments of the disclosure, the polymer prepared from the resin composition can be

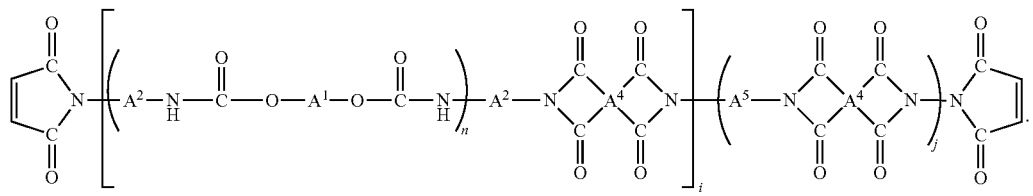

According to embodiments of the disclosure, the resin composition can further include an organic polymer material in order to improve the mechanical strength and chemical resistance of the cured product of the resin composition, wherein the organic polymer material can be epoxy resin, phenol formaldehyde resin, hydrocarbon resin, acrylic acid resin, polyamide, polyimide, poly(methyl methacrylate) (PMMA), polyvinylpyrrolidone (PVP), polystyrene, or polyvinylidene fluoride (PVDF). According to embodiments of the disclosure, the amount of the organic polymer material can be about 0.5 wt % to 150 wt %, based on the total weight of the polymer of the disclosure and the anhydride.

According to embodiments of the disclosure, the resin composition of the disclosure can optionally further include other components, such as known by those skilled in the art additive, in order to improve the physical properties of the cured product of the resin composition. The conventional additive includes, but not limited to, flame retardant, viscosity modifier, thixotropic agent, defoamer, leveling agent, surface treatment agent, stabilizer, and antioxidant. The additive can be used alone or in combination. The amount of the additive is not limited and can be optionally modified by a person of ordinary skill in the field.

According to embodiments of the disclosure, the components of the resin composition of the disclosure (including the compound of the disclosure and anhydride, or further including diamine, organic polymer material, and additive) can be further dissolved in a solvent, in order to adjust the viscosity of the resin composition, thereby facilitating a coating of the resin composition formed on a substrate via a coating process. The solvent can be any inert solvent that can dissolve or disperse the components of the disclosure, but does not react with the components. For example, the solvent which can dissolve or disperse the components of the composition include but are not limited to ethyl lactate, cyclohexanone, cyclopentanone (CPN), triglyme, 1,3-dimethyl-2-imidazolidinone (DMI), N-methyl-2-pyrrolidone (NMP), methyl ethyl ketone (MEK), N,N-dimethylacetamide (DMAc), γ-butyrolactone (GBL), N,N-dimethylformamide (DMF), or dimethyl sulfoxide (DMSO). The solvent can be used alone or in combination. The amount of the solvent is not particularly limited as long as the components of the resin composition can be evenly dissolved or dispersed therein. The method for coating the resin composition can be screen printing, spin coating, bar coating, blade coating, roller coating, dip coating, spray coating, or brush coating.

According to embodiments of the disclosure, the disclosure also provides a laminated substrate. The FIGURE is a schematic view of a laminated substrate 100 of an embodiment of the disclosure. As shown in the FIGURE, the laminated substrate 100 includes a conductive layer 10 (having a top surface 11 and a bottom surface 13) and a layer 20 disposed on the top surface 11 of the conductive layer 10, wherein the layer 20 is prepared by the aforementioned resin composition via a curing process (i.e. the layer can be the cured product of the resin composition).

According to embodiments of the disclosure, the conductive layer includes, but not limited to, a conductive metal foil. The conductive metal foil includes, but not limited to, copper foil, nickel foil or aluminum foil. In general, the thickness of the conductive layer can be about 0.1 μm to 100 μm, but the disclosure is not limited thereto. The surface of the conductive metal foil can be smooth or roughened (via a surface roughening treatment). According to embodiments of the disclosure, the surface of the conductive layer can have an average surface roughness (i.e. ten-point average surface roughness (Rz)) less than or equal to about 10 μm, such as less than or equal to about 5 μm, or less than or equal to about 2 μm. According to embodiments of the disclosure, the ten-point average surface roughness (Rz) is measured by a method in accordance with JIS B-0601 (1994) with a surfcorder (ET-3000).

According to embodiments of the disclosure, the laminated substrate can further include an insulating substrate (not shown), wherein the conductive layer can be disposed on the insulating substrate via the layer. Suitable material of the insulating substrate can be epoxy resin, phenol formaldehyde resin, hydrocarbon resin, acrylic acid resin, polyamide, polyimide, poly(methyl methacrylate) (PMMA), polyvinylpyrrolidone, polystyrene, polyvinylidene fluoride (PVDF), or a combination thereof. According to embodiments of the disclosure, the insulating substrate can further include a reinforcing material.

According to embodiments of the disclosure, the method for preparing the laminated substrate of the disclosure can include following steps. First, a resin composition is provided. Next, a coating of the resin composition is formed on a conductive metal foil via a coating process. Next, the coating is subjected to a curing process to form a layer (such as polyimide film or polyurethane-polyimide film). The temperature of the curing process can be about 200° C.-400° C., and the process time period can be 30 minutes to 8 hours. In addition, before subjecting the coating to a curing process, the coating can be subjected to a baking process in order to remove the solvent of the resin composition. According to embodiments of the disclosure, in the curing process, the resin composition undergoes an imidization (i.e. dehydrating cyclization) to form a cured product including polyimide (or polyurethane-polyimide).

Below, exemplary embodiments will be described in detail so as to be easily realized by a person having ordinary knowledge in the art. The inventive concept may be embodied in various forms without being limited to the exemplary embodiments set forth herein.

EXAMPLES

Resin Composition

Example 1

10 parts by mole of dihydric alcohol (commercially available from CRODA with a trade number of Pripol™

2033), 20 parts by mole of isophorone diisocyanate (IPDI), and N-methyl-2-pyrrolidone (NMP) were added into a reaction bottle, obtaining a solution (with a solid content about 5 wt %). Next, the aforementioned solution was reacted at 140° C. for 4 hours, obtaining a solution having the compound of the disclosure. Next, 100 parts by mole of 4,4'-biphthalic dianhydride (BPDA) was added into the solution having the compound of the disclosure. After stirring at 160° C. for 2 hours, 90 parts by mole of m-tolidine (m-TB) was added at room temperature. After stirring for 12 hours, Resin composition (1) was obtained.

Example 2

5 parts by mole of dihydric alcohol (commercially available from CRODA with a trade number of Pripol™ 2033), 10 parts by mole of isophorone diisocyanate (IPDI), and N-methyl-2-pyrrolidone (NMP) were added into a reaction bottle, obtaining a solution (solid content about 5 wt %). Next, the aforementioned solution was reacted at 140° C. for 4 hours, obtaining a solution having the compound of the disclosure. Next, 100 parts by mole of 4,4'-biphthalic dianhydride (BPDA) was added into the solution having the compound of the disclosure. After stirring at 160° C. for 2 hours, 95 parts by mole of m-tolidine (m-TB) was added at room temperature. After stirring for 12 hours, Resin composition (2) was obtained.

Example 3

30 parts by mole of dihydric alcohol (commercially available from CRODA with a trade number of Pripol™ 2033), 60 parts by mole of isophorone diisocyanate (IPDI), and N-methyl-2-pyrrolidone (NMP) were added into a reaction bottle, obtaining a solution (solid content about 5 wt %). Next, the aforementioned solution was reacted at 140° C. for 4 hours, obtaining a solution having the compound of the disclosure. Next, 100 parts by mole of 4,4'-biphthalic dianhydride (BPDA) was added into the solution having the compound of the disclosure (the molar ratio of BPDA to the compound of the disclosure was about 2). After stirring at 160° C. for 2 hours, 70 parts by mole of m-tolidine (m-TB) was added at room temperature. After stirring for 12 hours, Resin composition (3) was obtained.

Example 4

75 parts by mole dihydric alcohol (commercially available from CRODA with a trade number of Pripol™ 2033), 150 parts by mole of isophorone diisocyanate (IPDI), and N-methyl-2-pyrrolidone (NMP) were added into a reaction bottle, obtaining a solution (solid content about 5 wt %). Next, the aforementioned solution was reacted at 140° C. for 4 hours, obtaining a solution having the compound of the disclosure. Next, 150 parts by mole of maleic anhydride (MA) was added into the solution having the compound of the disclosure (the molar ratio of maleic anhydride to the compound of the disclosure was about 2). After stirring at 160° C. for 2 hours, Resin composition (4) was obtained.

Comparative Example 1

40 parts by mole of dihydric alcohol (commercially available from CRODA with a trade number of Pripol™ 2033), 80 parts by mole of isophorone diisocyanate (IPDI), and N-methyl-2-pyrrolidone (NMP) were added into a reaction bottle, obtaining a solution (solid content about 5 wt %). Next, the aforementioned solution was reacted at 140° C. for 4 hours, obtaining a solution having the compound of the disclosure. Next, 100 parts by mole of 4,4'-biphthalic dianhydride (BPDA) was added into the solution having the compound of the disclosure. After stirring at 160° C. for 2 hours, 60 parts by mole of m-tolidine (m-TB) was added at room temperature. After stirring for 12 hours, Resin composition (5) was obtained.

Comparative Example 2

10 parts by mole of diamine (commercially available from Croda Japan Co., Ltd. with a trade number of Priamine 1075), 90 parts by mole of m-tolidine (m-TB), 100 parts by mole of 4,4'-biphthalic dianhydride (BPDA), and N-methyl-2-pyrrolidone (NMP) were added into a reaction bottle, obtaining a solution (solid content about 5 wt %). Next, after reacting the solution at 160° C. for 12 hours, Resin composition (6) was obtained.

Comparative Example 3

100 parts by mole of m-tolidine (m-TB), 100 parts by mole of 4,4'-biphthalic dianhydride (BPDA), and N-methyl-2-pyrrolidone (NMP) were added into a reaction bottle, obtaining a solution (solid content about 5 wt %). Next, after reacting the solution at 160° C. for 12 hours, Resin composition (7) was obtained.

Comparative Example 4

100 parts by mole of 4,4'-oxydianiline (4,4'-ODA), 100 parts by mole of p-phenylene bis(trimellitate) dianhydride (TAHQ), and N-methyl-2-pyrrolidone (NMP) were added into a reaction bottle, obtaining a solution (solid content about 5 wt %). Next, after reacting the solution at 160° C. for 12 hours, Resin composition (8) was obtained.

The components for preparing Resin compositions (1)-(8) of Examples 1-4 and Comparative Examples 1-4 were shown in Table 1.

TABLE 1

| | Example 1 | Example 2 | Example 3 | Example 4 | Comparative Example 1 | Comparative Example 2 | Comparative Example 3 | Comparative Example 4 |
|---|---|---|---|---|---|---|---|---|
| Pripol ™ 2033 (parts by mole) | 10 | 5 | 30 | 75 | 40 | — | — | — |
| IPDI (parts by mole) | 20 | 10 | 60 | 150 | 80 | — | — | — |

TABLE 1-continued

| | Example 1 | Example 2 | Example 3 | Example 4 | Comparative Example 1 | Comparative Example 2 | Comparative Example 3 | Comparative Example 4 |
|---|---|---|---|---|---|---|---|---|
| BPDA (parts by mole) | 100 | 100 | 100 | — | 100 | 100 | 100 | — |
| TAHQ (parts by mole) | — | — | — | — | — | — | — | 100 |
| MA (parts by mole) | — | — | — | 150 | — | — | — | — |
| Priamine 1075 (parts by mole) | — | — | — | — | — | 10 | — | — |
| m-TB (parts by mole) | 90 | 95 | 70 | — | 60 | 90 | 100 | — |
| 4,4'-ODA (parts by mole) | — | — | — | — | — | — | — | 100 |

Properties Measurement of the Cured Product of the Resin Composition

Resin composition (1)-(8) were coated on a copper foil by blade coating to form coatings (thickness can be about 18 μm) individually. Next, the coating was baked at 100° C. for 30 minutes in order to remove solvent (NMP). Next, the copper foil with the coating was subjected to an imidization (dehydrating cyclization) under nitrogen atmosphere at 350° C. for 60 minutes, obtaining the copper foil with a layer (including the cured product of the resin composition). Next, the peel strength of the copper foil with the layer was measured, and the results are shown in Table 2. The peel strength was measured by an universal tensile testing machine (AGS-X, SHIMADZU) according to IPC™-650 2.4.8 (90° peel strength).

Finally, the copper foil was removed by etching process, obtaining the layer including the cured product of the resin composition.

Next, the moisture absorption rate, dielectric coefficient (Dk) and dielectric loss factor (Df) of the layer prepared from Resin compositions (1)-(8) before and after water absorption were measured, and the chemical resistance of the layer prepared from Resin compositions (1)-(8) was measured, and the results are shown in Table 2. The moisture absorption rate was determined using the following equation: moisture absorption rate=$(W_1-W_0)/W_0 \times 100\%$, wherein $W_0$ refers to the weight of the layer after baking at 100° C. for 1 hour and cooling to room temperature, and $W_1$ refers to the weight of the layer after immersing in water for 24 hours. The dielectric coefficient (Dk) and dielectric loss factor (Df) were measured at a frequency of 10 GHz using a microwave dielectrometer (available from AET Corporation). The dielectric coefficient (Dk) and dielectric loss factor (Df) of the layer after water absorption were measured by immersing the layer in water for 24 hours. The chemical resistance was determined by following steps. The layer was immersed in methyl ethyl ketone (MEK) at 70° C. for 10 minutes, followed by washing with water for 5 minutes. Thereafter, when a deformation of shape or a variation of thickness of the layer was observed, the test was marked with X. Otherwise, it was marked with O.

TABLE 2

| | moisture absorption rate | before water absorption Dk/Df | after water absorption Dk/Df | peel strength (kg/cm) | chemical resistance |
|---|---|---|---|---|---|
| Example 1 | 0.52 | 3.15/0.0048 | 3.24/0.0055 | 0.86 | O |
| Example 2 | 0.60 | 3.23/0.0052 | 3.42/0.0061 | 0.81 | O |
| Example 3 | 0.48 | 3.12/0.0045 | 3.31/0.0054 | 1.12 | O |
| Example 4 | 0.38 | 2.57/0.0052 | 2.6/0.0057 | 1.23 | O |
| Comparative Example 1 | 0.45 | 2.62/0.0051 | 2.71/0.0060 | 1.25 | X |
| Comparative Example 2 | 0.50 | 3.21/0.005 | 3.24/0.006 | 0.65 | O |
| Comparative Example 3 | 1.80 | 3.52/0.007 | 3.68/0.015 | 0.45 | O |
| Comparative Example 4 | 0.97 | 3.65/0.005 | 3.71/0.0128 | 0.51 | O |

As shown in Table 1 and Table 2, in the resin compositions of Examples 1-4 and Comparative Example 1, when the molar ratio of the compound of the disclosure to the diamine is within a range of 1:19 to 3:7, the chemical resistance of the cured product of the resin composition can be improved on the premise that the dielectric coefficient and dielectric loss factor of the cured product of the resin composition are not deteriorated and the moisture absorption rate of the cured product of the resin composition is not increased.

As shown in Comparative Example 2, when replacing the compound of the disclosure with a diamine having a high carbon number (Priamine 1075), the dielectric coefficient and dielectric loss factor of the cured product (layer) of the resin composition are not obviously affected, but the adhesion between the obtained layer and the copper foil is obviously reduced, resulting in the layer being easy to peeled off of the copper foil. As shown in Comparative Examples 3 and 4, when replacing the compound of the disclosure with a diamine (m-TB or 4,4'-ODA), the moisture absorption rate, dielectric coefficient and dielectric loss factor of the cured product (layer) of the resin composition are obviously increased. In addition, the layer is apt to peel off of the copper foil.

It will be clear that various modifications and variations can be made to the disclosed methods and materials. It is intended that the specification and examples be considered as exemplary only, with the true scope of the disclosure being indicated by the following claims and their equivalents.

What is claimed is:

1. A resin composition, comprising:
a compound, wherein the compound has a structure represented by Formula (I):

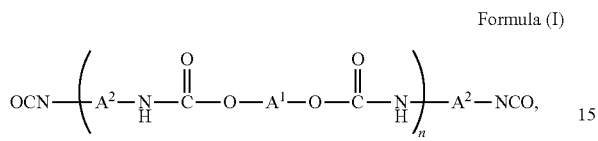

Formula (I)

wherein $A^1$ is $C_{24-48}$ alkylene group, $C_{24-48}$ alkenylene group, $C_{24-48}$ alkynylene group, $C_{24-48}$ alicyclic alkylene group, $C_{24-48}$ alicyclic alkenylene group, or $C_{24-48}$ alicyclic alkynylene group; $A^2$ can be $C_{2-12}$ alkylene group, $C_{6-25}$ arylene group, $C_{4-8}$ cycloalkylene group, $C_{5-25}$ heteroarylene group, divalent $C_{7-25}$ alkylaryl group, divalent $C_{7-25}$ acylaryl group, divalent $C_{6-25}$ aryl ether group, or divalent $C_{7-25}$ acyloxyaryl group; and, n≥1; and
an anhydride, wherein the anhydride comprises monoanhydride, dianhydride, or a combination thereof.

2. The resin composition as claimed in claim 1, wherein $A^1$ is a linear group, branched group, or branched cyclic group and has a chemical formula of —$C_nH_{2n}$—, —$C_nH_{2(n-1)}$—, —$C_nH_{2(n-2)}$—, —$C_nH_{2(n-3)}$—, —$C_nH_{2(n-4)}$—, —$C_nH_{2(n-5)}$—, or —$C_nH_{2(n-6)}$—, wherein n is 24 to 48.

3. The resin composition as claimed in claim 1, wherein the $A^2$ is

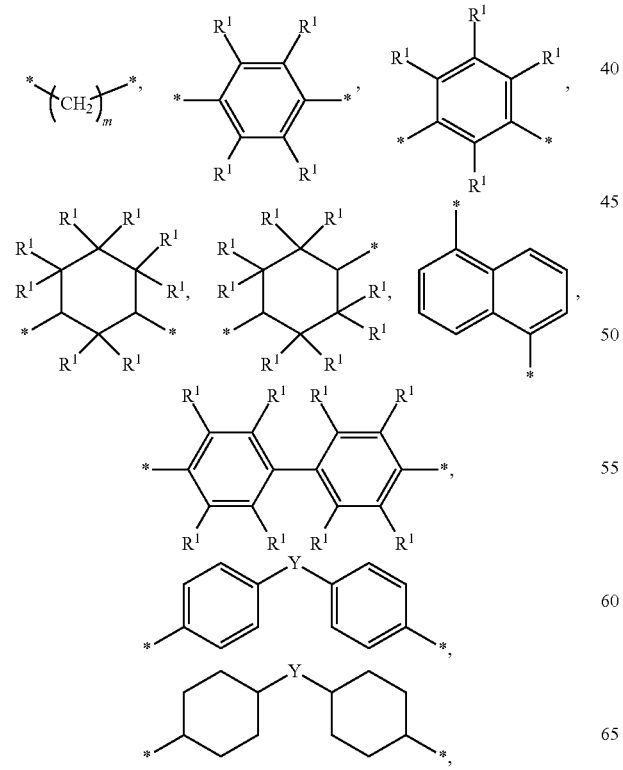

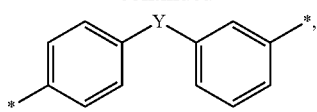

or; Y is —O—, —C($R^1$)$_2$-,

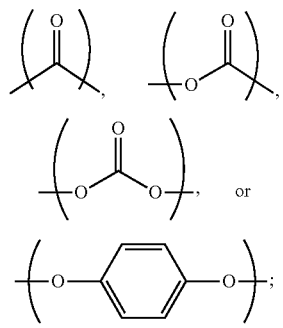

$R^1$ are independently hydrogen, fluorine, $C_{1-6}$ alkyl group, or $C_{1-6}$ fluoroalkyl group; and, m is 2, 3, 4, 5, 6, 7, or 8.

4. The resin composition as claimed in claim 1, wherein $A^1$ is

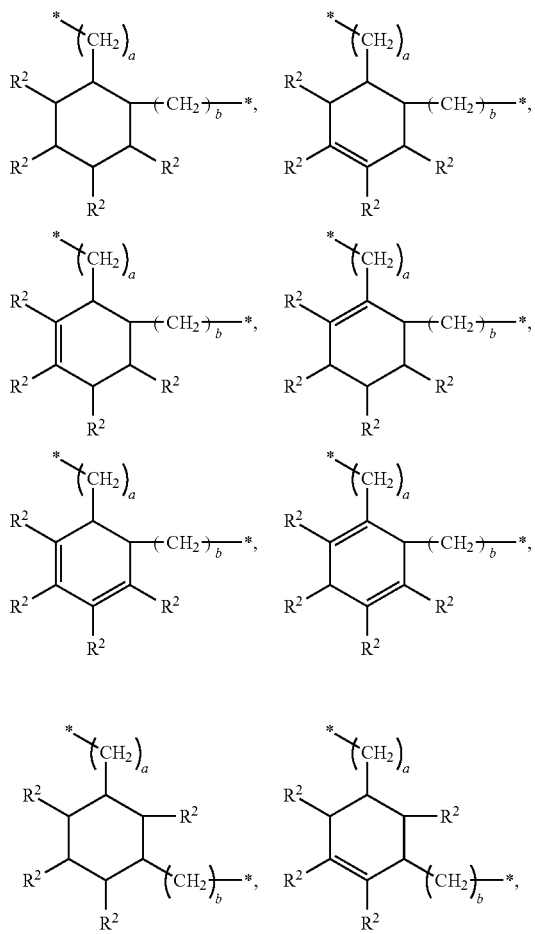

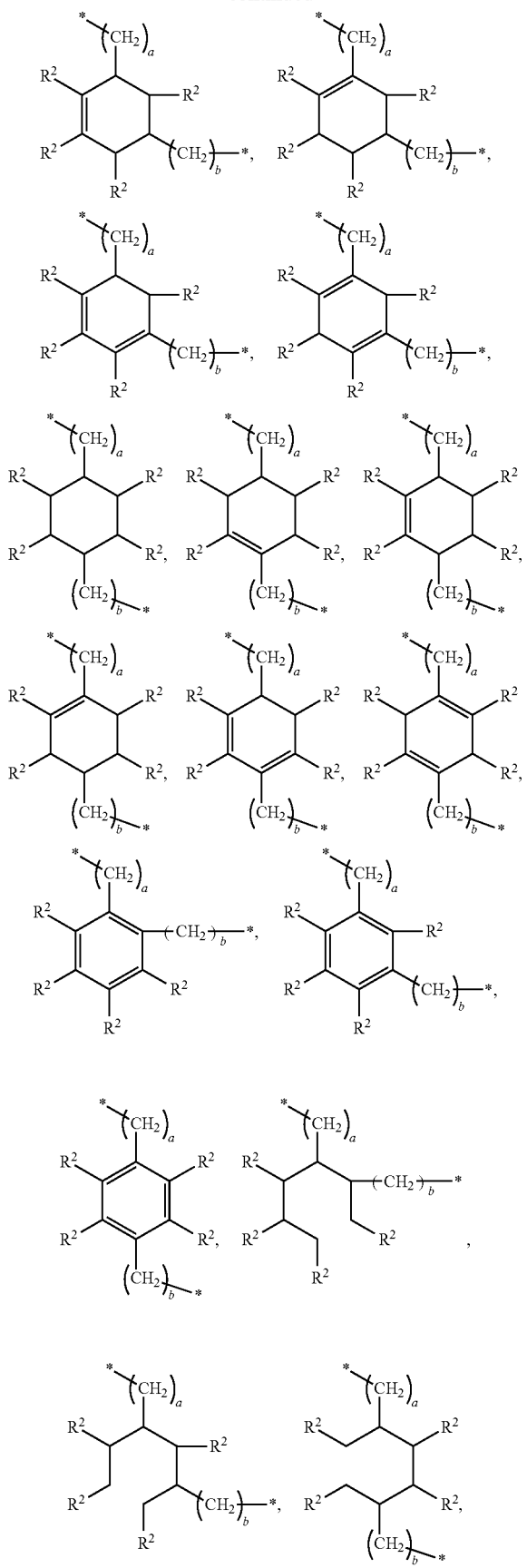

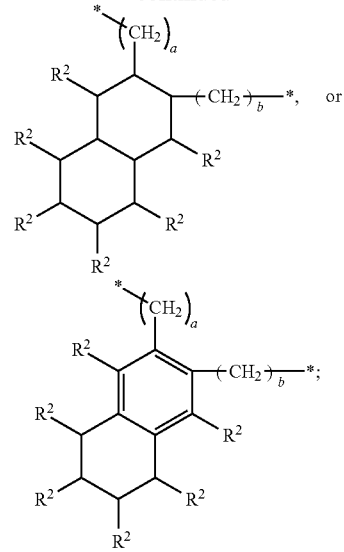

12≥a≥4; 12≥b≥4; $R^2$ is independently hydrogen, $C_{4-10}$ alkyl group, $C_{4-10}$ alkenyl group, or $C_{4-10}$ alkynyl group; at least two $R^2$ are not hydrogen; and, $A^1$ has 24-48 carbon atoms.

5. The resin composition as claimed in claim 1, when the anhydride is monoanhydride, the anhydride has a mole number $M^1$, and the compound has a mole number $M^2$, wherein $1.5 \leq M^2/M^1 \leq 2.5$.

6. The resin composition as claimed in claim 1, when the anhydride is dianhydride, the anhydride has a mole number $M^1$, and the compound has a mole number $M^2$, wherein $0.05 \leq M^2/M^1 \leq 1$.

7. The resin composition as claimed in claim 1, when the anhydride is a combination of monoanhydride and dianhydride, the anhydride has a mole number $M^1$, and the compound has a mole number $M^2$, wherein $0.05 \leq M^2/M^1 \leq 3$, and the molar ratio of the monoanhydride to the dianhydride is 1:99 to 99:1.

8. The resin composition as claimed in claim 1, wherein the monoanhydride is maleic anhydride, succinic anhydride, styrene maleic anhydride, 5-norbornene-2,3-dicarboxylanhydride, 3,6-epoxy-1,2,3,6-tetra hydrophthalicanhydride, 3,4,5,6-tetrahydrophthalic anhydride, phthalic anhydride, 1,2,3,6-tetrahydrophthalic anhydride, itaconic anhydride (IA), citraconic anhydride (CA), or 2,3-dimethylmaleic anhydride (DMMA).

9. The resin composition as claimed in claim 1, wherein the dianhydride is

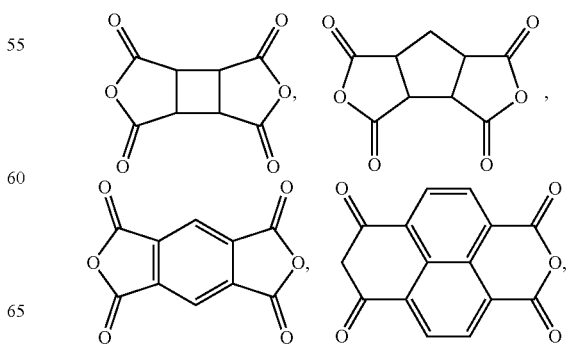

-continued

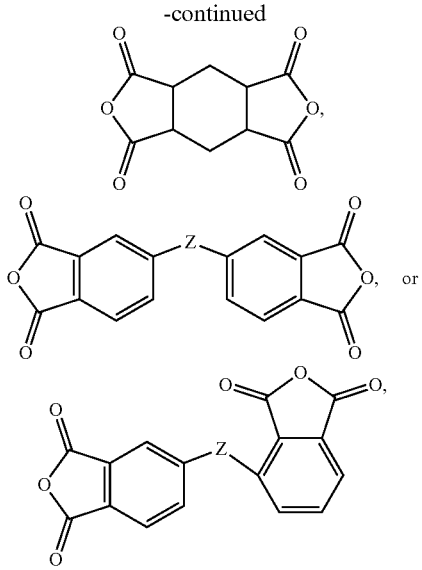

wherein Z is single bond, —O—, —SO$_2$—, —C(CH$_3$)$_2$—, —C(CF$_3$)$_2$—,

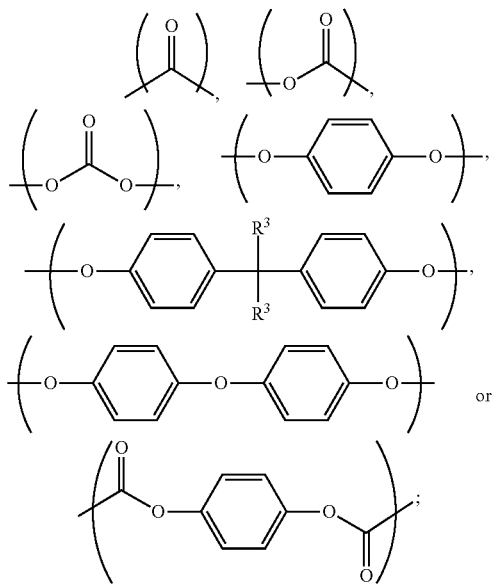

and, R$^3$ are independently hydrogen, C$_{1-6}$ alkyl group, or C$_{1-6}$ fluoroalkyl group.

10. The resin composition as claimed in claim 1, wherein the dianhydride is pyromellitic dianhydride (PMDA), 4,4'-(hexafluoroisopropylidene)-diphthalic anhydride (6FDA), 4,4'-oxydiphthalic anhydride (ODPA), 1,3-bis(4-aminophenoxy)benzene (RODA), 4,4'-biphthalic dianhydride (BPDA), 4,4'-bisphenol A dianhydride (BPADA), p-phenylene bis(trimellitate) dianhydride (TAHQ), hydroquinnone diphtalic anhydride (HQDA), or a combination thereof.

11. The resin composition as claimed in claim 1, when the anhydride is dianhydride, or the anhydride is a combination of monoanhydride and dianhydride, further comprising:
a diamine compound, wherein the anhydride has a mole number M$^1$, the compound has a mole number M$^2$, and the diamine compound has a mole number M$^3$, wherein $0.5 \le (M^2+M^3)/M^1 \le 3$, and $0.1 \le M^2/(M^2+M^3) \le 0.3$.

12. The resin composition as claimed in claim 11, wherein the diamine compound is

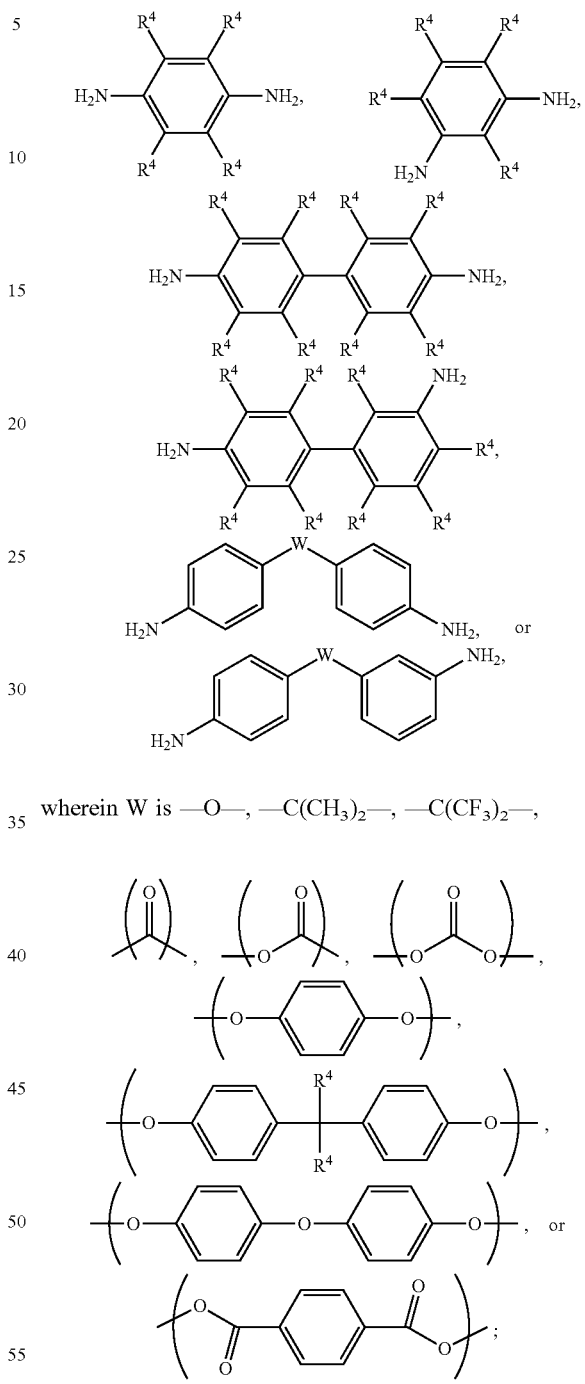

wherein W is —O—, —C(CH$_3$)$_2$—, —C(CF$_3$)$_2$—, and, R$^4$ is hydrogen, fluorine, C$_{1-6}$ alkyl group, or C$_{1-6}$ fluoroalkyl group.

13. The resin composition as claimed in claim 11, wherein the diamine compound is m-tolidine (m-TB), m-phenylenediamine (m-PDA), p-phenylenediamine (p-PDA), 4,4'-oxydianiline (4,4'-ODA), 3,4'-oxydianiline (3,4'-ODA), 1,4-bis(4-aminophenoxy)benzene (1,4-APB), 1,3-bis(4-aminophenoxy)benzene (1,3-APB), 1,2-bis(4-aminophenoxy)benzene (1,2-APB), 1,3-bis(3-aminophenoxy)benzene (APB-133), 2,5-bis(4- aminophenoxy)toluene, bis(4-[4-aminophenoxy]phenyl) ether (BAPE), 4,4'-bis[4-aminophenoxy]biphenyl (BAPB), 2,2-bis[4-(4-aminophenoxy)]phenyl propane (BAPP), bis-(4-(4-aminophenoxy)phenyl sulfone (BAPS), 2,2'-bis(trifluoromethyl) 4,4'-diaminobiphenyl (TFMB), 1,4-diaminobenzene (PPD), or a combination thereof.

14. A laminated substrate, comprising:
   a conductive layer having a surface; and
   a layer disposed on the surface of the conductive layer, wherein the layer comprises a cured product of the resin composition as claimed in claim 1.

15. The laminated substrate as claimed in claim 14, wherein the conductive layer is copper foil, nickel foil or aluminum foil.

\* \* \* \* \*